United States Patent
Büchner et al.

(10) Patent No.: US 9,550,726 B2
(45) Date of Patent: Jan. 24, 2017

(54) METHODS FOR DECOLORIZING COMPOSITIONS COMPRISING BETAINES

(71) Applicant: Lonza Ltd., Visp (CH)

(72) Inventors: Thomas Büchner, Naters (CH); Gesa Paradies, Brig (CH); Justin Yang, Guangzhou (CN)

(73) Assignee: LONZA LTD., Visp (CH)

( * ) Notice: Subject to any disclaimer, the term of this patent is extended or adjusted under 35 U.S.C. 154(b) by 0 days.

(21) Appl. No.: 14/431,861

(22) PCT Filed: Nov. 13, 2013

(86) PCT No.: PCT/EP2013/073682
§ 371 (c)(1),
(2) Date: Mar. 27, 2015

(87) PCT Pub. No.: WO2014/076110
PCT Pub. Date: May 22, 2014

(65) Prior Publication Data
US 2015/0251989 A1   Sep. 10, 2015

(30) Foreign Application Priority Data
Nov. 16, 2012   (EP) ..................... 12193048

(51) Int. Cl.
*C07C 227/40* (2006.01)

(52) U.S. Cl.
CPC .................. *C07C 227/40* (2013.01)

(58) Field of Classification Search
CPC .................................... C07C 227/40
See application file for complete search history.

(56) References Cited

U.S. PATENT DOCUMENTS

2009/0325246 A1   12/2009   Oishi et al.

FOREIGN PATENT DOCUMENTS

| CA | 2371210 | * | 11/2000 |
|---|---|---|---|
| CN | 101337902 A | | 1/2009 |
| CN | 101875616 A | | 11/2010 |
| DE | 1136711 B | | 9/1962 |
| DE | 19634640 A1 | | 3/1998 |
| EP | 2360141 A1 | | 8/2011 |
| JP | S6383199 A | | 4/1988 |
| JP | 2010143857 A | | 7/2010 |
| WO | WO9615274 A1 | | 5/1996 |
| WO | WO 98/08803 | * | 3/1998 |
| WO | WO2007003425 A2 | | 1/2007 |
| WO | WO2010089095 A1 | | 8/2010 |

OTHER PUBLICATIONS

Sanchez et al., Excerpt from "Trends in biotechnological production of fuel ethanol from different feedstocks", [Excerpt] pp. 5270-5274, Bioresource Technology 99 (2008).

Zhang et al., "Research on New Process for Extraction of Betaine from Fermentation Waste Liquid of Beet Molasses", Fine Chemicals, vol. 17, No. 3, Mar. 2000, pp. 1-6.

* cited by examiner

*Primary Examiner* — Shailendra Kumar
(74) *Attorney, Agent, or Firm* — Hoffmann & Baron, LLP

(57) ABSTRACT

The invention relates to a process for decolorizing a composition comprising a betaine comprising the steps of
  (a) providing a solution of the composition in an organic solvent,
  (b) contacting the solution with a decolorant, wherein the decolorant is a polar solid decolorant.
The invention also relates to uses of ion exchange materials and decolorized solutions and compositions obtainable by the inventive process.

23 Claims, No Drawings

METHODS FOR DECOLORIZING COMPOSITIONS COMPRISING BETAINES

This application is the U.S. National Phase of, and Applicants claim priority from, International Patent Application Number PCT/EP2013/073682 filed Nov. 13, 2013, which claims priority from EP 12193048.1 filed Nov. 16, 2012, each of which is incorporated herein by reference.

The invention relates to a process for decolorizing a composition comprising a betaine. The invention also relates to uses of polar solid decolorants for decolorizing solutions, and to compositions obtainable by the inventive process.

BACKGROUND OF THE INVENTION

Betaines are neutral chemical compounds with a positively charged cationic functional group, usually a quaternary ammonium or phosphonium group, and a negatively charged functional group, usually as a carboxylate group. A betaine is thus a zwitterion. Historically, the term "betaine" referred only to the specific compound N,N,N-trimethylglycine.

Many betaines are vitamins, pharmaceuticals or precursors thereof. They are used as food additives, diet components or pharmaceuticals. An important betaine is carnitine (vitamin Bt; 3-hydroxy-4-(trimethylammonio)butanoate). Carnitine is a quaternary ammonium compound biosynthesized from the amino acids lysine and methionine. Carnitine exists in two stereoisomers. The biologically active form is L-carnitine (levocarnitine, LC), whilst its enantiomer, D-carnitine, is biologically inactive. L-carnitine is an endogenous compound, which plays a key metabolic role, transporting long chain fatty acids into the mitochondria for energetic oxidation. Supplementation with acetyl-L-carnitine (ALC) has been shown to increase overall regional cerebral metabolism in rodents. Carnitine and its esters also have non-metabolic roles in brain function as neuroprotectants, antioxidants and modulators of neurotransmission.

Betaines, such as carnitine, are usually produced by organic synthesis at an industrial scale. Typically, solutions of betaines in solvents, for example in aqueous solution or in ethanol, are obtained. The solutions and solid products are subjected to purification steps for obtaining the betaine at high purity, thereby removing salts, solvent, residual starting products, side products and the like. Common purification steps comprise crystallization, recrystallization, washing of crystallized products, distillation, filtration and salt removal by ion exchange chromatography. As a result, highly concentrated betaines are obtained in solid form.

Typically, solid betaines, such as carnitine, are colorless and solutions thereof are likewise colorless and transparent. However, when such betaines are produced by organic synthesis, and even when purified thereafter, often colorized products are obtained. For example, carnitine produced by organic synthesis usually has a brown or yellow coloration. The reason for the coloration is not precisely known.

Methods in the art for producing carnitine usually comprise a decoloration step, wherein a solution comprising the carnitine product is contacted with activated carbon. Activated carbon (active carbon, activated charcoal, activated coal) is a non-polar adsorbent capable of binding large amounts of non-polar substances due to its high internal surface. After sufficient incubation time, a colorless solution is obtained, whilst compounds causing the coloration are absorbed by the carbon. Betaines are not bound to the activated carbon and thus decolorized. For example, the problem of colorized carnitine products and decoloration with activated carbon are disclosed in WO2007/003425 A2 (page 2, lines 14 to 22), US 2009/0325246 (section [0100]) or EP 2 360 141 A1 (section [0039]).

In the state of the art, ion exchange chromatography is applied for desalting aqueous solutions of compositions comprising L-carnitine and converting L-carnitine salts into the inner salt. CN101337902 A discloses a method for purifying L-carnitine from aqueous solutions, in which pre-desalting steps are carried out with electroosmosis and an anion exchange material, where after a decoloring treatment is carried out with activated carbon.

CN101875616 discloses another method for producing L-carnitine, wherein a desalting step is carried out with an ion exchange material.

Decolorization of betaine solutions with activated carbon has certain drawbacks. At first, activated carbon is relatively costly, especially when used in a large-scale industrial process. Columns, which are packed with activated carbon, cannot be recycled efficiently. The efficiency of decoloration is not always sufficient and relatively large amounts of activated carbon are required for quantitative decoloration. Trace amounts of carbon may remain in the product and may interfere with subsequent reactions or uses, for example when subsequent reactions are carried out with sensitive catalysts.

Moreover, decolorization with activated carbon, although efficient in aqueous solutions, is not efficient in some organic solvents, such as ethanol. However, synthesis of betaines in ethanol is an important industrial process. Thus there is a need for efficient decoloring of betaines directly in such solutions in organic solvents.

WO96/15274 relates to methods for decolorizing aqueous solutions in the sugar industry, which comprise high amounts of sugars and may comprise additional N,N,N-trimethylammonioacetat ("betaine"). The inventors suggest decoloration of the sugar solutions with polyaluminum chlorides.

DE 1 136 711 relates to methods for extracting N,N,N-trimethylammonioacetat ("betaine") from natural products, such as sugar rich juices and molasses. The process is carried out with aqueous sugar-rich solutions and requires several consecutive ion exchange treatment steps with cation and anion exchange resins.

DE 196 34 640 A1 relates to methods for desalting aqueous solutions comprising precursors for the production of L-carnitine. The method comprises at least electrodialysis and cation exchange chromatography. The method does not relate to decoloration of the solutions. Further, it is relatively complicated and requires long treatment times of about 8 to 12 days.

It would be desirable to provide a process for decoloring betaines and betaine solutions, especially carnitine and carnitine solutions, which overcome the above mentioned problems. Specifically, it would be desirable to provide a process which does not require a decoloration treatment with activated carbon, and which is also efficient in organic solvents.

Problem Underlying the Invention

The problem underlying the invention is to provide processes, uses and decolorized compositions, which overcome the above-mentioned problems. Specifically, the problem underlying the invention is to provide a method for decolorizing betaines, especially carnitine, without a decoloration step with carbon. The inventive process shall allow effective decolorization of compositions and solutions whilst being relatively simple, and being efficient in the presence of organic solvents. Chemicals and devices required for the decolorization shall be easily available at low costs and applicable for industrial large scale purification processes. The decolorization shall be applicable within a relatively short time. Specifically, it shall be applicable for solutions of purified betaines obtained in organic synthesis processes, for example for solutions of L-carnitine in alcohols.

DISCLOSURE OF THE INVENTION

Surprisingly, the problem underlying the invention is solved by the processes, uses and compositions according to the claims. Further inventive embodiments are disclosed throughout the description.

Subject of the invention is a process for decolorizing a composition comprising a betaine comprising the steps of
 (a) providing a solution of the composition in an organic solvent,
 (b) contacting the solution with a decolorant, wherein the decolorant is a polar solid decolorant.

The inventive process is also a process for producing a decolorized composition comprising a betaine. Decolorization of a composition can be monitored by known methods, preferably by determining the transparency of the solution. In the inventive process, the coloration of a colorized or at least slightly colorized starting solution, for example a brown or yellow solution, is reduced or eliminated. Preferably, the product solution obtained thereby is colorless, as solid betaine obtained from such a solution after solvent removal. The invention relates to any process, in which the transparency of the solution is increased and colorization is decreased.

Pure betaine solutions, such as L-carnitine solutions, should be colourless since the betaines are colourless. However, such solutions tend to have undesired coloration, often yellow or brown. This is especially a problem with betaine solutions and betaines, which are a product of a preceding organic synthesis. Colorization seems to be conferred to betaines and betaine solutions by impurities. However, it is not known precisely which impurities colorize betaine solution. Such impurities seem to be removed during the inventive process with a polar solid decolorant. This was unexpected, because in the art non-polar activated carbon is used for decolorization.

In a preferred embodiment of the invention, the process comprises a subsequent step of
 (c) maintaining the solution for a time period sufficient for decoloring the solution.

In principle, a time period is considered sufficient, in which a desired degree of decolorization is achieved. Preferably, the time period is of sufficient length to obtain a fully decolorized, transparent solution. Preferably, the transparency of the solution after step (c) is more than 70%, more preferably more than 80%, most preferably more than 90% or more than 95%. Transparency is preferably determined at 430 nm in a 50 mm cuvette. The betaine solution may be a standard solution of 10% (w/w) betaine in the respective solvent, such as ethanol. Typically, the time period for decoloration may be between 5 minutes and 20 hours, preferably between 20 minutes and 8 hours or between 30 minutes and 4 hours. Preferably, the transparency of a betaine solution is increased at least by 10%, more preferably at least by 20% or by 50%, preferably when carrying out the inventive process with 5 wt. % solid decolorant for 30 min. Specifically, this increase of transparency may be observed for the solution obtained after step (b), after step (c) or after step (d), when compared to the starting solution provided in step (a).

In a preferred embodiment, in step (c) the solution is moved mechanically, for example by stirring, shaking or swaying. When keeping the solution in motion, intimate contact of the ion exchange material with the solution is supported, thereby increasing decolorization speed. When carrying out the process in a column, the running speed is adapted such that the average contact time is sufficient.

In a preferred embodiment of the invention, the process comprises a subsequent step
 (d) separating the polar solid decolorant from the solution.

Preferably, the polar solid decolorant is removed by mechanical separation, for example by sedimentation, filtration and/or centrifugation. Alternatively, the solid may be removed within a device, such as a sieve, which is withdrawn from the solution after a sufficient time period for decoloration.

In a preferred embodiment, the polar solid decolorant is provided in a column and the solution is passed through the column. The column dimensions and running conditions, such as column length and flow, are adapted such that the eluate is decolorized sufficiently. Decoloration may be improved by using two or more columns in series.

In the inventive process, the betaine does not bind, or essentially does not bind to the solid decolorant. In contrast, typical betaine impurities seem to be bound to the polar solid decolorant and are removed together with the solid decolorant from the solution, where after a decolorized solution is obtained. According to the invention, the overall process may comprise introduction of the polar solid decolorant into the solution, incubation for a sufficient time to reach decoloration and separation of the solid decolorant from the solution. Additional steps used in column purification processes in the art, such as binding of betaines and elution with specific buffers, are not required.

In a preferred embodiment of the invention, the solid decolorant is recycled. Recycling can be carried out by treating the material with washing solution. Appropriate washing solutions could have a high salt concentration and/or comprise additives, such as detergents, for eluting impurities and recovery.

In a preferred embodiment of the invention, the process comprises after step (d) a subsequent step of
 (e) removing the solvent from the solution to obtain a solid decolorized composition.

The solvent can be removed from the solution by methods known in the art, for example by distillation. Preferably, the solvent is recycled, i. e. recovered and reused in the process. In a specific embodiment, steps (b) to (e), or steps (b) to (d), are carried out in consecutive order without additional purification steps in between these steps.

After removal of the solvent, a solid decolorized composition is obtained. The composition comprises, or essentially consists of, the betaines. It may be subjected to additional purification steps, for example for removing residual solvent or residual solid decolorant. For example, the solid composition may be dried, recrystallized, and the like. In another preferred embodiment of the invention, the product, which is the solid dry composition, is processed further. It may be processed into a desired constitution, size and shape. For example, it may be converted into a powder, granulate or tablets, optionally in a mixture with other components, such as processing aids and/or vitamins.

The inventive process may be a batch process or continuous process. In a continuous process, the solution passes the polar solid decolorant continuously.

As used herein, the term "betaine" refers to a generic group of chemical compounds. A betaine is a neutral chemical compound with a single cationic quaternary functional group, preferably a quaternary ammonium or phosphonium group, and a single anionic functional group, such as a carboxylate group. The anionic and cationic charge is permanent. Thus the cationic group does not comprise an acidic hydrogen atom attached to the N or P atom. The betaine is thus a zwitterion. Preferably, the betaine comprises a single quaternary ammonium group and a single quaternary carboxylate group. The generic term "betaine" comprises, but does not specifically refer to the specific compound N,N,N-trimethylglycine.

Preferably, the betaine used according to the invention is an inner salt. It does not comprise, or essentially does not comprise an additional anion, such as chloride, or an additional cation, such as H$^+$ or ammonium. Carboxyl groups are essentially in the ionic form. However, a minor portion, for example below 2%, below 0.5% or below 0.2% (w/w) may be in the acidic form.

According to the invention, the betaine is preferably not a polymer. In other words, it is not product of a polymerization process from repetitive monomer units. It is preferably a low molecular weight substance. Preferably, the molecular weight is below 500, below 400 or below 300 g/mol.

In a preferred embodiment, the betaine is an ester, the betaine comprising a single hydroxyl group which is esterified, preferably with an alkyl group having 1 to 20 carbon atoms, more preferably between 1 and 6 carbon atoms.

In a preferred embodiment of the invention, the betaine is a compound of formula (I):

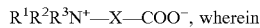

$R^1R^2R^3N^+$—X—COO$^-$, wherein $R^1$, $R^2$ and $R^3$ are alkyl groups having 1 to 6 carbon atoms, which are selected independently from each other, and X is an alkandiyl group having 1 to 6 carbon atoms, which is linear or branched, which is preferably methandiyl, 1,2-ethandiyl or 1,3-propandiyl, the alkandiyl group being optionally substituted, preferably with a residue selected from —OH, —NH$_2$, —SH, —O—NHR$^4$ and —O—COR$^4$, wherein R$^4$ is preferably an alkyl group having 1 to 20 carbon atoms, which may be linear or branched, more preferably methyl, ethyl, n-propyl, isopentyl or n-dodecyl.

Preferably, $R^1$, $R^2$ and/or $R^3$ is methyl and/or ethyl. Preferably, $R^1R^2R^3N^+$— is a trimethylammonium group. Preferably, the betaine is optically active.

In highly preferred embodiments of the invention, the betaine is L-carnitine, N,N,N-trimethylglycine or an acylated L-carnitine. Preferably, the acylated L-carnitine is an ester of L-carnitine and a carbonic acid having 1 to 20 carbon atoms, which is preferably not branched. Preferably, the acylated L-carnitine is acetyl-L-carnitine (ALC), propionyl-L-carnitine (PLC), isovaleryl-L-carnitine or lauroyl-L-carnitine.

In a preferred embodiment, the composition provided in step (a) essentially consists of the betaine. However, relatively small amounts of impurities may be present, which confer coloration to the composition and to the solution, in which the composition is dissolved. In a preferred embodiment, the composition is a direct or intermediate product from organic synthesis of the betaine, possibly with subsequent purification steps. Preferably, it is already substantially free from salts, side products, starting products and the like. Preferably, salts were removed in a preceding desalting step. The desalting step may comprise any common method, such as dialysis, osmosis, ultrafiltration, nanofiltration, distillation, extraction, crystallization, microfiltration and the like. Preferably, the desalting step comprised electrodialysis, as disclosed for example by WO2010/089095, especially as in examples 1 and 2 thereof.

In a preferred embodiment of the invention, the composition in step (a) comprises more than 50,%, more than 75%, more than 95%, preferably more than 98%, more than 99.5% or more than 99.8% (w/w) of the betaine, especially L-carnitine, based on the total amount of all solid components. More preferably, the composition in step (a) comprises more than 95% L-carnitine, based on the total amount of all solid components. In a preferred embodiment of the invention, the composition in step (a) comprises less than 1%, preferably less than 0.2% or less than 0.05% (w/w) of salts, based on the total amount of all solid components. Specifically, such salts may be chlorides, acetates or cyanides. In a specific embodiment, the solution was subjected to a preceding desalting step.

In a preferred embodiment, the composition in step (a) is a product of an organic synthesis reaction for producing the betaine, especially L-carnitine. More preferably, the product is a crude reaction product, which has not been pre-purified, or which has only been desalted before. Typically, such a reaction product comprises the betaine, side products and residual unreacted starting materials. Often, such crude reaction products have an undesired color. The side products and residual starting materials are often structurally related to the betaine. Therefore, decolorization of such organic reaction products is relatively difficult.

In a preferred embodiment, the betaine, such as the L-carnitine, is not a natural product and/or not purified from a natural product. In other words, it is not extracted from natural products, for example from sugar rich biological materials. Preferably, the composition provided in step (a) does not comprise sugars, or less than 0.1% (w/w) or less than 1% (w/w) sugars, based on the overall solids.

Preferably, the solution provided in step (a) consists of the solid composition and the organic solvent.

The solvent is an organic solvent, preferably a polar organic solvent, such as an alcohol, ether or ester. In a highly preferred embodiment, the solvent is an aliphatic alcohol, more preferably one comprising 1 to 6 carbon atoms, such as methanol, ethanol, isopropanol or butanol. Most preferably, the solvent is ethanol. The solvent may also be a mixture of organic solvents, for example a mixture of ethanol with another organic solvent, for example one comprising up to 90% (w/w) or up to 50% (w/w) ethanol. In a preferred embodiment of the invention, the solution in step (a) comprises 5 to 75%, preferably 10 to 50%, more preferably 15 to 40% (w/w) of the betaine composition, the rest being solvent.

Organic solvents, such as ethanol, may comprise low amounts of water. According to the invention, the organic solvent, especially ethanol, may comprise low levels of water, for example less than 5% (w/w), less than 1% (w/w), less than 0.5% (w/w) or less than 0.1% (w/w). In specific embodiments, the solvent is technical grade ethanol, comprising between 2 and 4% (w/w) water, or absolute ethanol, comprising less than 1% (w/w) water, or even less than 0.1% (w/w) water.

In a preferred embodiment, the organic solvent does not comprise water, or does essentially not comprise water. The term "essentially" means that only inevitable impurities of water may be present.

According to the invention, decolorization of the betaine solution is mediated by a polar solid decolorant. As used herein, the term solid refers to room temperature (23° C.) and to a solid substance remaining after removal of all solvent. The solid decolorant is not dissolved during the process. At least the surface of the decolorant is polar. Polar substances have electric dipoles at the surface. Such solids are hydrophilic. Preferably, the polar solid is capable of forming hydrogen bonds in aqueous solution. Preferably, the polar solid comprises charged groups, more preferably cationic groups, and/or oxygen atoms on the surface.

According to the invention, it was found that betaine solutions in organic solvents, such as ethanol, are decolorized efficiently with polar solid decolorants. This was unexpected, because according to the state of the art decoloration was carried out with activated carbon, which is a non-polar adsorbent and thus tends to adsorb hydrophobic substances. Further, activated carbon, although being efficient in water, is considerably less efficient in decolorizing betaines in organic solvent, such as ethanol (see examples).

In a preferred embodiment of the invention, the polar solid decolorant is an ion exchange material. Typically, the surface of ion exchange materials comprises ionic groups, Lewis acidic and/or Lewis basic groups. The ion exchange material may be an anion exchange material, which is preferred, or a cation exchange material. It may also be an amphoteric exchange material, which is capable of exchanging both cations and anions. In addition, the ion exchange material may have adsorptive or absorptive characteristics. Mineral based ion exchangers comprising silicates, such as bentonite and Fuller's earth; or hydrotalcite, combine ion exchange properties with adsorptive properties. According to the invention, it was found that with various ion exchange materials, colorizing impurities can be removed efficiently from solutions comprising betaines. However, it is not known whether all impurities are removed by anion exchange interactions, or whether some impurities are also, or partly, removed by absorption or adsorption. Such interactions tend to interact and thus a clear distinction, although desirable in theory, is not always practically appropriate. Thus, the invention is not restricted to specific binding mechanisms.

Unlike activated carbon, common ion exchange materials, such as polymeric ion exchange resins or mineral-based silicates and hydrotalcite, are colorless. If at all, they release only trace amounts of impurities into the solutions, mostly traces of salts, which are usually acceptable for subsequent uses and applications. Thus, the use of the polar solid decolorants is advantageous for preparing betaine solutions or betaines.

In a preferred embodiment of the invention, the ion exchange material is an ion exchange resin, a silicate or hydrotalcite. The process may also use combinations of such ion exchange materials or combinations with other polar solid decolorant, or apply multiple consecutive decoloring steps with different ion exchange materials.

In a preferred embodiment of the invention, the ion exchange material is an ion exchange resin, more preferably an anion exchange resin. Such a resin is based on an organic polymer matrix. Preferably, the resin comprises ionic groups. Preferably, the ionic groups are positively charged. In a highly preferred embodiment, the groups are quaternary ammonium groups. The ionic groups are covalently linked to the matrix with appropriate spacers. Such anion exchange resins are known in the art and commercially available, for example from Dow Chemical/Rohm and Haas, US, under the trademark "Amberlite".

In another preferred embodiment, the ion exchange material is or comprises a silicate. Silicates comprise silicate groups, but may comprise also other inorganic groups, atoms and ions. Typically, silicate ion exchange materials are minerals or derived from minerals. In a preferred embodiment of the invention, the mineral is or comprises bentonite, montmorillonite and talc, or is derived from such a mineral. Such minerals are known in the art and commercially available. Bentonite is based on aluminium silicate, which comprises montmorillonite. Talc is a hydrated magnesium silicate. Montmorillonite is a hydrated sodium calcium aluminium magnesium silicate hydroxide. In a preferred embodiment, the silicate comprises magnesium. Preferably, the mineral is Fuller's earth. Silicate-based ion exchange materials useful in the inventive process are commercially available, for example from Süd-Chemie, DE, under the trademarks "Tonsil" or EXM1607. In a preferred embodiment, the pH of the silicate, especially the bentonite, when dissolved in water, is above 5, more preferably about 5 to 9.

Bentonites are known and available with variations in composition and properties. According to the invention, it was found that decoloration of betaines is efficient in organic solvents with various bentonites. However, especially good results were obtained when using a bentonite comprising about 65 to 75% $SiO_2$, about 8 to 12% $Al_2O_3$, about 3 to 5% MgO and about 2 to 4% $Fe_2O_3$ (all percentages are weight %). Preferably, this bentonite has a pH above 5, such as between 5 and 9, when dissolved in water. Such a bentonite is available under the trademark EXM1607 from Süd-Chemie, DE.

In another preferred embodiment, the ion exchange material is or comprises hydrotalcite. Hydrotalcite is a layered double hydroxide of general formula $(Mg_6Al_2(CO_3)(OH)_{16} \cdot 4(H_2O)$. Hydrotalcite has anion exchange capabilities. It is commercially available, for example under the trademark Sorbacid 911 from Süd-Chemie, DE. In a preferred embodiment, the pH of the hydrotalcite, when suspended in water, is above 7, more preferably about 7 to 11.

Hydrotalcites are known and available with variations in composition and properties. According to the invention, it was found that decoloration of betaines is efficient in organic solvents with various hydrotalcites. However, especially good results were obtained when using a hydrotalcite comprising about 15 to 25% $Al_2O_3$ and about 30 to 40% MgO (all percentages are weight %). Preferably, this hydrotalcite has a pH above 7, more preferably about 7 to 11, when suspended in water. Such a preferred hydrotalcite is available under the trademark Syntal HAS 696 from Süd-Chemie, DE.

Methods are known in the art for increasing the ion exchange capability and also absorptive properties of such minerals. The ion exchange capability can be increased by chemical treatments. In a preferred embodiment of the invention, the mineral is pre-activated by an acid treatment. Acid treatments, also referred to as "acid activation", affect the outer and inner surfaces and acidity of such minerals, yielding products with a specific pore structure and a specific distribution of cationic and anionic groups on the surface. Fullers earth is obtained by acidic activation of minerals, usually from bentonite. It is used in the art for purifying oils and lipids.

In another preferred embodiment of the invention, the polar solid decolorant is or comprises an alkaline earth metal oxide. The alkaline earth metal oxide may consist of the alkali metal and oxygen, or may comprise other metal cations and anions. It may also comprise other components, such as crystal water. Preferably, the alkaline earth metal oxide is magnesium oxide or calcium oxide. Surprisingly, a very effective and rapid decoloration was observed in the presence of magnesium oxide. This is advantageous, because magnesium oxide is colorless and inexpensive.

In a preferred embodiment of the invention, the polar solid decolorant is an inorganic material, such as a mineral, such as a silicate or hydrotalcite, or an alkali metal oxide.

In the inventive process, a decoloration step with carbon, especially activated carbon, is not necessary. Thus it is preferred that the overall process does not comprise a use of molecular carbon or activated carbon for decolorization. In an embodiment of the invention, the decolorant is not a polyaluminum chloride.

The polar solid decolorant may be provided in any appropriate form, such as a powder, granules, pellets, a solid block and the like. Preferably, the solid decolorant has a high internal surface area, and thus a high contact surface. Thus a fine powder and/or a porous structure may be advantageous.

Subject of the invention is also the use of a polar solid decolorant, which is preferably an ion exchange material and/or an alkaline earth metal oxide, for decolorizing a composition comprising betaines, preferably L-carnitine. Subject of the invention is also the use of a process of the invention for decolorizing a composition comprising betaines, preferably L-carnitine.

Preferably, the inventive process is also a process for decolorizing betaines, preferably L-carnitine, or for decolorizing solution comprising betaines, preferably L-carnitine.

Another subject of the invention is a decolorized solution or composition, obtainable by an inventive process. According to the invention, it is possible to obtain a decolorized solution or composition of pure or substantially pure betaine or L-carnitine. The inventive solution or composition is distinct from typical decolorized solutions or compositions of pure betaines or carnitine, because no residual traces of activated carbon are comprised. This is advantageous for possible subsequent reactions or uses, which could be impaired by traces of carbon, for example sensitive reactions in the presence of catalysts.

The inventive process solves the problem underlying the invention. The invention provides a simple and effective process for the decolorization of betaines, such as L-carnitine, which is effective also in the presence of organic solvent. A solution is decolorized simply by contacting with a polar solid material, especially an ion exchange material and/or an alkaline earth metal oxide. Mineral based ion exchange materials, such as Fuller's earth, are easily available in large amounts and significantly cheaper than activated carbon. Thus the use of such materials provides a significant cost advantage in industrial large scale processes for the production of betaines, compared to conventional processes using activated carbon. Activated carbon used in the art for decolorizing betaines does not comprise ionic, acidic or basic groups on the surface. Thus, it could not be assumed that efficient decolorization could be achieved by simply contacting a solution of the betaine with ion exchange material

EXAMPLES

General Methods

Transparency of L-carnitine solutions was determined at 430 nm in 50 mm cuvettes and evaluated according to U.S. Pharmacopeia (USP) chapter 1061.

Examples 1 to 6

Decolorization with Ion Exchange Materials

An L-carnitine solution was decolorized with various ion exchange materials in batch processes. The L-carnitine was a crude product obtained by organic synthesis having a brownish to yellowish coloration. An ethanolic L-carnitine solution was prepared with 20.39% (w/w) L-carnitine concentration. Transparency was determined to be 20.3%. In a flask equipped with a magnetic stir bar and reflux condenser, 80 g of the ethanolic L-carnitine solution and 6.25 wt. % of the ion exchange resin were charged. The anion exchange resins used comprised a cross-linked polystyrene matrix with quaternary ammonium groups (trademark Amberlite FPA90CI and FPA98CI; Dow Chemical, US). The mixture was stirred for the given time at 60° C. before the resin was removed by filtration. Carnitine concentration and transparency of solutions obtained thereby were measured. The conditions and results are summarized in table 1 below.

TABLE 1 conditions and results of examples 1 to 6

| Example | Resin | Time [h] | Conc. [% w/w] | Transp. [%] |
| --- | --- | --- | --- | --- |
| 1 | Amberlite FPA98Cl | 0.5 | 20.49 | 67.2 |
| 2 | Amberlite FPA98Cl | 1.0 | 20.63 | 68.2 |
| 3 | Amberlite FPA98Cl | 1.5 | 20.71 | 70.6 |
| 4 | Amberlite FPA90Cl | 0.5 | 20.53 | 71.8 |
| 5 | Amberlite FPA90Cl | 1.0 | 20.51 | 71.9 |
| 6 | Amberlite FPA90Cl | 1.5 | 20.43 | 71.6 |

Example 7

Ion Exchange Chromatography

L-carnitine solution was decolorized in a continuous process by anion exchange chromatography. A double jacket reactor (500 ml) was provided with an internal stirrer. A double jacket column (diameter: 15 mm; length: 460 mm) was provided underneath the reactor. The solution from the reactor was applied to the column inlet at the head of the column through a connection. A collecting vessel was positioned underneath the column outlet for collecting the eluate. A thermostat each kept the temperature in the reactor and in column at 60° C. The anion exchange resin comprised a cross-linked polystyrene matrix with quaternary ammonium groups (trademark Amberlite FPA 90CI; Dow Chemical, US). The resin was pre-treated by washing with 2000 ml deionized water followed by washing with 500 ml anhydrous ethanol. 50 g fresh resin was filled into the double jacket column and washed with the given washing solutions, where after the column was warmed up to 60° C. The L-carnitine used was a crude product obtained by organic synthesis having a brownish to yellowish coloration. A feed solution of L-carnitine in ethanol was filled into a reactor, heated to 60° C. and applied with an average flow rate of 6-7 g/min to the column. A colorless eluate was collected. In total, 24 kg of carnitine in ethanol coming from three batches (batch 1: 7.6 kg L-carnitine in ethanol, transparency=64.3%; batch 2: 8.5 kg L-carnitine in ethanol, transparency=81%; batch 3: 7.8 kg L-carnitine in ethanol, transparency=63.8%) were treated as described. The yield after anion exchange chromatography was 100%. A colorless solution (transparency>95%) was obtained.

Examples 8 to 28

Further examples were carried out with various materials to assess their capability of decoloring L-carnitine solutions. Solutions of L-carnitine were combined with various solid materials and the colors of the solutions were monitored. Comparative examples 8 and 9 were controls without decoloring materials. Examples 10 and 11 were comparative examples with activated carbon. Examples 12 to 19 were carried out with various polar anion exchange materials. Comparative examples 20 to 22 were carried out with non-polar ion exchange or adsorbent materials. Example 23 was carried out with a cation exchange material. Examples 24 and 25 were carried out with alkaline metal oxides. Comparative examples 26 to 28 were carried out with other inorganic compounds. Solutions of L-carnitine in water (40% w/w) and ethanol (10-25% w/w) were prepared. The L-carnitine was a crude product obtained from organic synthesis, having a brownish to yellowish coloration. The solution was heated to 40° C. The initial transparency of the solutions was determined (430 nm, 50 mm cuvette), and determined as <7% for EtOH and 4% in water. The decoloring materials were added (3% w/w), mixed and kept at 40° C. for two hours. After two hours, the ion exchange material was removed by filtration and the transparency was determined. The ion exchange materials, properties of the materials and results are summarized in Table 2 below. The compositions and properties of the hydrotalcites and bentonites are summarized in Table 3 below.

No decolorization was observed in the control experiments with water or ethanol alone. Strong decolorization was observed with various polar materials, which are anion exchange resins, silicates, hydrotalcite, magnesium oxide and calcium oxide. In comparative examples, it was found that activated carbon is efficient in water, but of low efficiency in ethanol. Also other materials with non-polar surfaces are not efficient (examples 20 to 22).

TABLE 2

Ion exchange materials and results.

| Ex. | Solid Material | Trademark, Supplyer | Supplyer | Properties | Solvent | Transp. [%] | Decolor. |
|---|---|---|---|---|---|---|---|
| 8 (C) | — | — | — | control | EtOH | 7 | none |
| 9 (C) | — | — | — | control | water | <4% | none |
| 10 (C) | activated carbon | Norit DX-1 | Norit, NL | — | water | 92.7 | very good |
| 11 (C) | activated carbon | GAC 1240 Plus | Norit, NL | acid washed, steam activation, pH 5-8 | EtOH | 35.4 | low |
| 12 | hydrotalcite | Sorbacid 911 | Süd-Chemie, DE | Al—Mg-carbonate*hydroxide, basic | EtOH | 69.0 | good |
| 13 | hydrotalcite | Syntal HSA 696 | Süd-Chemie, DE | Al—Mg-carbonate*hydroxide, basic | EtOH | 93.1 | very good |
| 14 | bentonite | Tonsil Supreme 112 FF | Süd-Chemie, DE | pH 2-8, acid leached | EtOH | 39.5 | low |
| 15 | bentonite | EXM1607 | Süd-Chemie, DE | non activated clay, pH 6-11, | EtOH | 80.2 | very good |
| 16 | bentonite | Tonsil 570 FF | Süd-Chemie, DE | pH 6-11 | EtOH | 52.6 | low |
| 17 | bentonite | Tonsil Optimum 210 FF | Süd-Chemie, DE | pH 2-8, acid leached | EtOH | 38.6 | low |
| 18 | anion exchange | Amberlite FPA98CI | Rohm and Haas, US | quaternary amine function, Cl-form, for large organic molecules | EtOH | — | good |
| 19 | anion exchange | Amberlite FPA90CI | Rohm and Haas, US | quaternary amine function, Cl-form, for large organic molecules | EtOH | 70.3 | good |
| 20 (C) | anion exchange | Amberlite FPX66 | Rohm and Haas, US | non functionalized, aromatic polymer | EtOH | — | none |
| 21 (C) | ion exchange | Amberlite XAD 761 | Rohm and Haas, US | non functionalized, phenol-formaldehyde polymer | EtOH | — | none |
| 22 (C) | polymeric absorbent | Amberlite XAD 7HP | Rohm and Haas, US | non ionic, aliphatic crosslinked polymer | EtOH | — | none |
| 23 (C) | cation exchange | Amberlite FPC22H | Rohm and Haas, US | sulfonic acid, H+-form | EtOH | — | none |
| 24 | MgO | | | basic | EtOH | 94.0 | instantly |
| 25 | CaO | | | basic | EtOH | 36.0 | low |
| 26 (C) | NaOH | | | basic | EtOH | — | none |
| 27 (C) | $MgCl_2$ | | | | EtOH | — | none |
| 28 (C) | $Na_2CO_3$ | | | basic | EtOH | — | none |

Transp. = transparency;
(C) = comparative example

TABLE 2

Compositions and properties of decolorants used in examples 12 to 17

| Ex. | Trademark | pH | BET $m^2/g$ | $SiO_2$ | $Al_2O_3$ | MgO | $Fe_2O_3$ | $TiO_2$ | $CO_2$ | CaO | $Na_2O$ | $K_2O$ | $Cl^-$ | $SO_4^-$ | Annealing loss | total |
|---|---|---|---|---|---|---|---|---|---|---|---|---|---|---|---|---|
| 12 | Sorbacid 911 | 7.0-9.5 (5% susp. in EtOH) | ≤15 | | 12 | 22 | | | | | | | | | | |
| 13 | Syntal HSA 696 | 10 (5% susp. in water) | >17 | — | 20.5 | 34.0 | | | 9.5 | | 0.1 | | 0.1 | 0.2 | | 64 |

TABLE 2-continued

Compositions and properties of decolorants used in examples 12 to 17

| Ex. | Trademark | pH | BET $m^2/g$ | $SiO_2$ | $Al_2O_3$ | MgO | $Fe_2O_3$ | $TiO_2$ | $CO_2$ | CaO | $Na_2O$ | $K_2O$ | $Cl^-$ | $SO_4^-$ | Annealing loss | total |
|---|---|---|---|---|---|---|---|---|---|---|---|---|---|---|---|---|
| 14 | Tonsil Supreme 112 FF | 2-4 (10% solution) | 190 | 70.2 | 9.4 | 2.5 | 2.8 | 0.3 | | 2.3 | 0.4 | 1.5 | | | 9.5 | 98.9 |
| 15 | EXM1607 | 6-8 (10% solution) | 220 | 70.1 | 10 | 4.3 | 3 | | | 1.5 | 0.3 | 1.4 | | | 8.6 | 99.2 |
| 16 | Tonsil 570 FF | | | 58.6 | 5.3 | 23.8 | 2.1 | 0.2 | | 0.8 | 0.2 | 0.9 | | | | |
| 17 | Tonsil Optimum 210 FF | 2.2-4.8 | 200 | 66.8 | 14.2 | 2.3 | 3.7 | | | 1.1 | 0.8 | 2.2 | | | 8 | 99.1 |

The invention claimed is:

1. A process for decolorizing a composition comprising a betaine selected from L-carnitine and acylated L-carnitine comprising the steps
   (a) providing a solution of the composition in a polar organic solvent,
   (b) contacting and decoloring the solution with a decolorant, wherein the decolorant is a polar solid decolorant selected from an ion exchange material and/or an alkaline earth metal oxide.

2. The process of claim 1, comprising a subsequent step
   (c) maintaining the solution for a time period sufficient for decoloring the solution.

3. The process of claim 1, comprising a subsequent step
   (d) separating the solid decolorant from the solution.

4. The process of claim 3, comprising a subsequent step
   (e) removing the solvent from the solution to obtain the solid decolorized composition.

5. The process of claim 1, wherein the solvent is an alcohol.

6. The process of claim 1, wherein the betaine is a compound of formula $R^1R^2R^3N^+$—X—$COO^-$, wherein
   $R^1$, $R^2$ and $R^3$ are alkyl groups having 1 to 6 carbon atoms, which are selected independently from each other, and
   X is an alkandiyl group having 1 to 6 carbon atoms, which is linear or branched.

7. The process of claim 1, wherein the betaine is L-carnitine.

8. The process of claim 1, wherein the composition in step (a) comprises more than 95% (w/w) of the betaine, based on the total amount of all solid components.

9. The process of claim 1, wherein the solution in step (a) comprises 5 to 50% (w/w) of the composition.

10. The process of claim 1 wherein the ion exchange material is an ion exchange resin, a silicate or hydrotalcite, and/or wherein the alkaline earth metal oxide is magnesium oxide or calcium oxide.

11. The process of a claim 1 wherein the ion exchange resin is an anion exchange resin.

12. The process of claim 1 wherein the silicate is or comprises a mineral selected from bentonite, montmorillonite, talc, or is derived from such a mineral.

13. The process of claim 1, wherein the composition in step (a) is a product of an organic synthesis reaction for producing the betaine.

14. The process of claim 1, wherein the transparency of the betaine solution is increased at last by 10%, when compared to the transparency of the starting solution provided in step (a).

15. A decolorized solution or composition obtainable by a process of claim 1.

16. The process of claim 2, comprising a subsequent step
   (d) separating the solid decolorant from the solution.

17. The process of claim 16, comprising a subsequent step
   (e) removing the solvent from the solution to obtain the solid decolorized composition.

18. The process of claim 5 wherein the solvent is ethanol.

19. The process of claim 6 wherein said alkandiyl group is substituted.

20. The process of claim 19 wherein said alkandiyl group is substituted with a residue selected from —OH, —$NH_2$, —SH, —O—$NHR^4$, and —O—$COR^4$, wherein $R^4$ is an alkyl group having 1 to 20 carbon atoms.

21. The process of claim 1, wherein said composition in step (a) comprises more than 98% or more than 99.5% (w/w) of the betaine, based on the total amount of all solid components.

22. The process of claim 11 wherein said anion exchange resin comprises quaternary ammonium groups.

23. The process of claim 10 wherein said silicate comprises a mineral derived from bentonite, montmorillonite, talc, or is derived by pre-activation by acid treatment.

* * * * *